U S009322801B2

(12) United States Patent
Pratt et al.

(10) Patent No.: US 9,322,801 B2
(45) Date of Patent: Apr. 26, 2016

(54) APPARATUS AND METHOD OF REGENERATING ELECTROCHEMICAL GAS SENSORS

(75) Inventors: Keith Francis Edwin Pratt, Portsmouth (GB); Terence Nicholas Moran, Portsmouth (GB); Martin Jonathan Kelly, Clanfield (GB); John Chapples, Portsmouth (GB)

(73) Assignee: Honeywell International Inc., Morris Plains, NJ (US)

( * ) Notice: Subject to any disclaimer, the term of this patent is extended or adjusted under 35 U.S.C. 154(b) by 1402 days.

(21) Appl. No.: 12/776,689

(22) Filed: May 10, 2010

(65) Prior Publication Data

US 2010/0288652 A1  Nov. 18, 2010

Related U.S. Application Data

(60) Provisional application No. 61/178,284, filed on May 14, 2009.

(51) Int. Cl.
*G01N 27/26* (2006.01)
*G01N 27/416* (2006.01)
*G01N 27/404* (2006.01)

(52) U.S. Cl.
CPC .......... *G01N 27/4163* (2013.01); *G01N 27/404* (2013.01)

(58) Field of Classification Search
USPC ............. 204/424–429; 205/775, 783.5–785.5
See application file for complete search history.

(56) References Cited

U.S. PATENT DOCUMENTS

| 4,960,497 | A | * | 10/1990 | Gallagher | ................ 205/785.5 |
| 5,538,620 | A | | 7/1996 | Nikolskaja | |
| 5,690,808 | A | * | 11/1997 | Akmal et al. | ................. 205/775 |
| 5,958,214 | A | * | 9/1999 | Nikolskaja | ................... 205/784 |
| 7,175,753 | B2 | | 2/2007 | Kiesele et al. | |
| 2003/0192781 | A1 | * | 10/2003 | Kiesele et al. | ............... 204/424 |
| 2005/0194264 | A1 | | 9/2005 | Dalmia | |
| 2008/0000779 | A1 | | 1/2008 | Wang et al. | |
| 2008/0202944 | A1 | | 8/2008 | Santoli et al. | |

FOREIGN PATENT DOCUMENTS

DE  102 15 909 C1  10/2003

OTHER PUBLICATIONS

European Search Report corresponding to Application No. EP 10 16 2584, dated Aug. 25, 2010.

(Continued)

*Primary Examiner* — Luan Van
*Assistant Examiner* — Steven Rosenwald
(74) *Attorney, Agent, or Firm* — Conley Rose, P.C.; Kristin Jordan Harkins

(57) ABSTRACT

A method of improving performance of electrochemical gas sensors includes cycling potentials applied to one or more of the electrodes of the respective sensor(s) to improve performance of a different electrode. In a process for treating a reference electrode, potentials can be applied to working and, or counter electrodes so as to modify the environment in the vicinity of the reference electrode. An apparatus can carry out the method automatically.

8 Claims, 4 Drawing Sheets

(56) References Cited

OTHER PUBLICATIONS

Trapp, T. et al., "Development of a coulometric CO2 gas sensor," Sensors and Actuators B., Elsevier Sequoia S.A., Lausanne, CH LNKD—DOI:10.1016/S0925-4005(98)00161-0, vol. 50, No. 2, Jul. 31, 1998, pp. 97-103, XP004144856; ISSN: 0925-4005, p. 101, left-hand column, fig. 2.

Abstract of DE10215909 (C1). English translation of abstract of DE10215909 (C1) is not available. Abstract of DE10215909 (C1) indicates that it was also published as U.S. Pat. No. 7,175,753.

* cited by examiner

APPARATUS AND METHOD OF REGENERATING ELECTROCHEMICAL GAS SENSORS

CROSS-REFERENCE TO RELATED APPLICATION

This application claims the benefit of the filing date of U.S. Provisional Application Ser. No. 61/178,284 filed May 14, 2009 and entitled "Method of Regenerating Electrochemical Gas Sensors". The '284 application is hereby incorporated herein by reference.

FIELD

The invention pertains to methods to improve performance of electrochemical gas sensors. More particularly, the invention pertains to apparatus and methods to cycle the potentials applied to one or more sensor electrodes to promote electrochemical processes to return a respective electrode or its operating environment to normal operating conditions.

BACKGROUND

Electrochemical gas sensors typically contain two or three electrodes—a sensing and combined counter/reference for two electrode sensors, or a sensing, counter and reference for three electrode sensors. The principles of such sensors-have been described in 'Liquid Electrolyte Fuel Cells', B S Hobbs, A D S Tantram and R Chan-Henry, Ch 6 in 'Techniques and Mechanisms In Gas Sensing', Eds P T Moseley, J O W Norris and D E Williams, pub Adam Hilger 1991.

Certain changes in the characteristics of any of the electrodes can result in degradation of sensor performance. For example, contamination, poisoning or changes in oxidation state of the working electrode can change its activity relative to target gases. Similar effects on the counter electrode can result in it needing to be polarized to a greater extent to maintain the required bias voltage between the sensing and reference electrodes. This in turn can be problematic as the control electronics may not be able to provide sufficient voltage, or the counter electrode may be driven to a potential where undesirable electrochemical effects occur, such as evolution of gases, or production of species which may diffuse to the reference or working electrodes.

This latter effect is particularly problematic due to the typically close proximity of the three electrodes in practical commercial sensors. The reference electrode used in commercial electrochemical gas sensors is typically a 'pseudo reference' and as such its reference potential can be affected by factors such as poisoning, or varying concentrations of species in the surrounding electrolyte. For example, changes in dissolved oxygen concentration around a platinum pseudo reference electrode can change the reference potential. Changes in the reference potential result in an equal change in the working electrode potential since the latter is controlled potentiostatically relative to the former. As a result, changes in the reference potential can change the activity of the working electrode as well as its surface state and long term stability resulting in changes in cross sensitivity, or in extreme cases unwanted evolution of gases such as hydrogen or oxygen.

The evolution of bubbles of gas on any of the three electrodes can also result in reduction of contact area with the electrolyte. On the sensing electrode the reduction in active area can result in reduction in gas sensitivity. On the counter electrode the reduction in contact area can result in the need for higher polarization voltage. On the reference electrode this effect might not be expected to have any affect as no significant current is drawn. However it is known that in practice changes in the surface area of reference electrodes can have effects on sensor performance.

A specific example of the problem is exemplified with a non-consumable electrochemical oxygen 'pump' sensor. On this sensor oxygen is consumed on the sensing electrode and evolved on the counter electrode. The reference electrode needs to be in electrochemical contact with the electrolyte and the other electrodes. As a result the oxygen concentration in the vicinity of the reference electrode may vary over time. It is desirable to control the oxygen concentration in the vicinity of the reference electrode or to maintain it below a certain limit. Too high a concentration results in an anodic shift in the reference potential, which causes a corresponding anodic shift in the working electrode potential. This gives rise to an immediate reduction in the activity of the working electrode, and may also result in longer term drift in the working electrode performance.

It is known from the prior art that an electrode can be 'cleaned up' electrochemically by biasing it/passing current through it. It is also known that metal electrodes (for example, platinum) can be 'cleaned' by cycling their potential in acid to oxidize then strip surface oxides.

DETAILED DESCRIPTION

Figure 1:
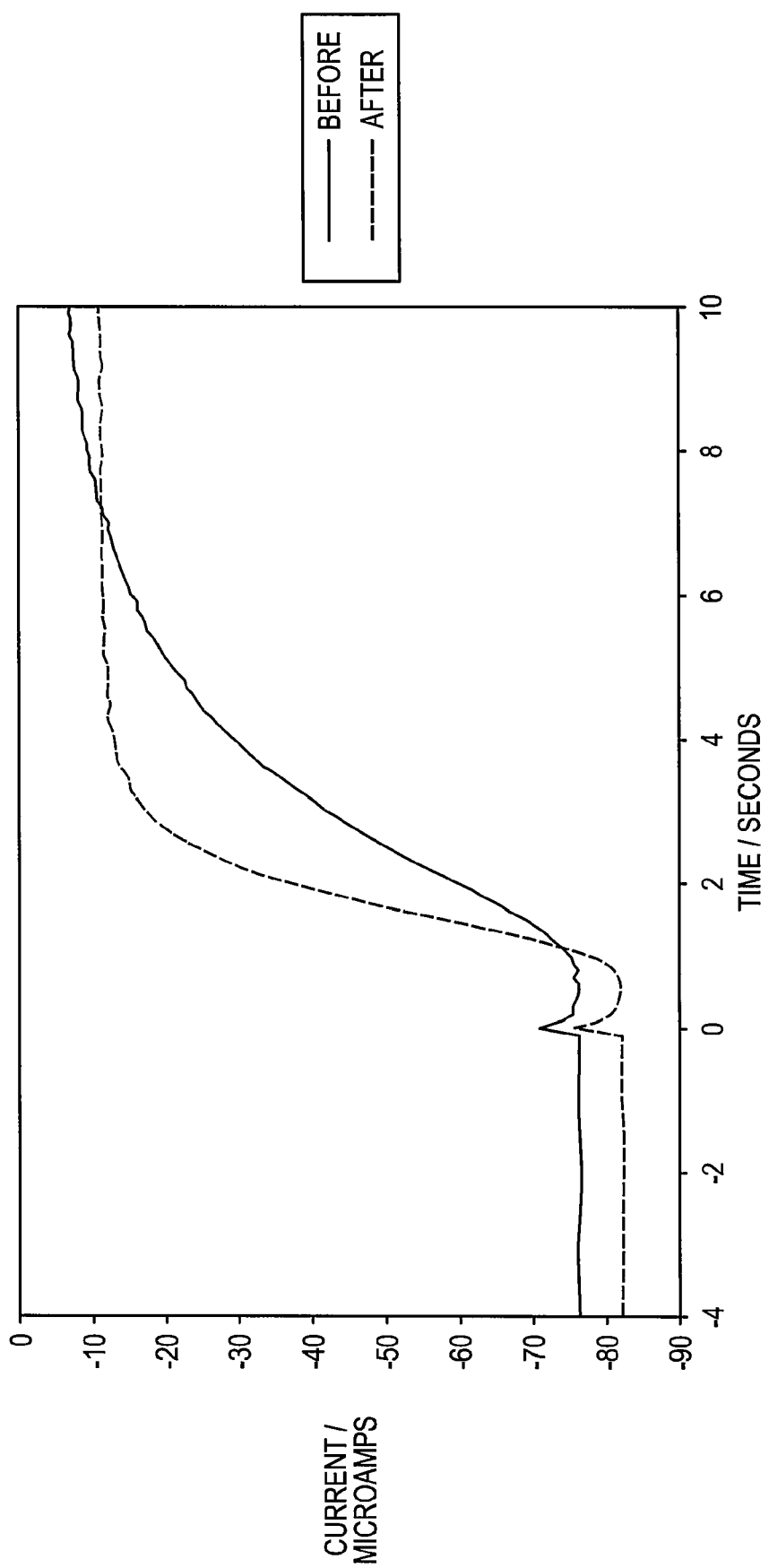
FIG. 1 is a graph that illustrates performance of an oxygen sensor before and after being processed with a method in accordance with the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In embodiments of the invention a method is provided of treating one or more of the electrodes, to return it to its correct operating state. The method, or process, involves changing the potentials applied to one or more of the other electrodes, to promote electrochemical processes which result in returning of a separate electrode or its operating environment to its normal operating conditions. This is of particular value for 'treating' the reference electrode since it is not desirable to pass a current through this electrode, however its environment can be changed by appropriate operation of other electrodes within the sensor. As no current is passed through the electrode its behavior as a reference is not compromised.

In other embodiments of the invention, an apparatus can implement a method of changing the potential applied to one or more of the electrodes as discussed above. In one aspect of the invention, the apparatus can include a programmable processor with contacts couplable to one or more gas sensors to be processed. Executable instructions, carried on a computer readable medium, can couple potentials to the electrodes to process one or more of the electrodes as discussed in more detail subsequently.

There are a number of scenarios in which sensor performance may have become degraded to a degree which can be reversed by appropriate modification of reference electrode environment.

One example is the removal of gases dissolved in the electrolyte (eg from the atmosphere). This can for example occur if the sensing electrode reaction is not capable of totally consuming the incoming gas. This may be because the sensing electrode has relatively poor activity towards the primary target species or because the incoming concentration is excessive, or could be because the incoming gas is a cross interferent towards which the sensing electrode is not designed to be especially active. In all cases, unconsumed gas may diffuse through the electrolyte to other parts of cell where it can interfere with normal operation, for example by altering reference electrode potential. Conventional ways of addressing such problems typically involve the use of scrubbing electrodes to consume excess gas. But these involve considerable additional cost and complication in cell construction and operation, hence are undesirable. One specific example of this is nitric oxide sensors where traditionally an auxiliary 'scrubbing' electrode is included to consume nitric oxide and/or partial reaction products which pass through the main working electrode and which would disturb the reference electrode potential if they reached it. The counter electrode could be used intermittently to scrub nitric oxide, removing the need for the fourth auxiliary electrode, simplifying sensor design and reducing cost.

Another example is relative to sensors for gases such as carbon monoxide where under unusual conditions of exposure to a very high concentration of the gas, not all of the target gas is consumed by the sensor, resulting in dissolved gas reaching the reference electrode, possibly changing its potential. One approach for removing the dissolved gas from the vicinity of the reference electrode is to 'overbias' the working electrode. This may not be desirable during normal operation due to cross sensitivity issues but may be acceptable as a short term 'clean up' phase.

A further example is where an interferent gas which the sensing electrode is not very active towards, for example hydrogen, dissolves in the electrolyte changing the environment of the reference electrode. Again this can be removed by appropriate operation of either the sensing or counter electrodes.

A further example of the application is the removal of gases dissolved in the electrolyte which are produced by the sensor itself—a specific example of this is discussed below:

For the specific example of the oxygen pump sensor described above, one method of reducing the oxygen concentration in the vicinity of the reference electrode is to intermittently operate the electrode amperometrically, driven to a potential where it consumes the oxygen itself, with two other electrodes acting temporarily as reference and counter electrodes. This approach may not be desirable as it requires changes to the configuration of the potentiostat circuitry and the reference electrode may take a long time to recover back to its correct potential. It is well known to those skilled in the art than passing current through reference electrodes is not desirable.

An alternative, and preferred, approach is to vary the potentials on the other electrodes so as to 'purge' the oxygen from the region of the reference electrode. If the excessive oxygen concentration is due to oxygen evolved from the counter electrode, then changing the bias conditions so that the counter electrode consumes rather than evolves oxygen can be used to reduce the oxygen concentration near to the reference electrode. In this case the working electrode temporarily acts as a counter electrode. This effect may be practically achieved simply by changing the bias voltage on the working electrode. In an oxygen pump sensor where, for example, the platinum sensing electrode is normally biased to, for example, −600 mV relative to the platinum pseudoreference electrode, and where the platinum counter electrode is normally in the region of +200 mV, it has been shown that setting the working electrode bias to 0V causes the counter electrode to swing to approximately −600 mV and therefore consumes oxygen.

Alternatively the counter electrode can be driven potentiostatically either by interchanging the electrode connections to the potentiostat, or using software, along with associated circuitry, to adjust the working electrode bias voltage such that the counter electrode is driven to the desired potential. Under these conditions the sensing electrode now temporarily evolves oxygen, however as there is typically a means of preventing oxygen reaching the working electrode from the other electrodes (so as to minimize background currents), the oxygen concentration in the vicinity of the reference electrode is determined more by the counter electrode than by the working electrode.

FIG. 1 illustrates the response of an oxygen pump sensor of the type described above, before and after processing in accordance with the invention. The solid line shows that the sensor has become slow to respond, due to changes in the environment of the reference electrode. The dashed line shows that following the 'cleaning up' process the speed of response has increased.

Figure 2:
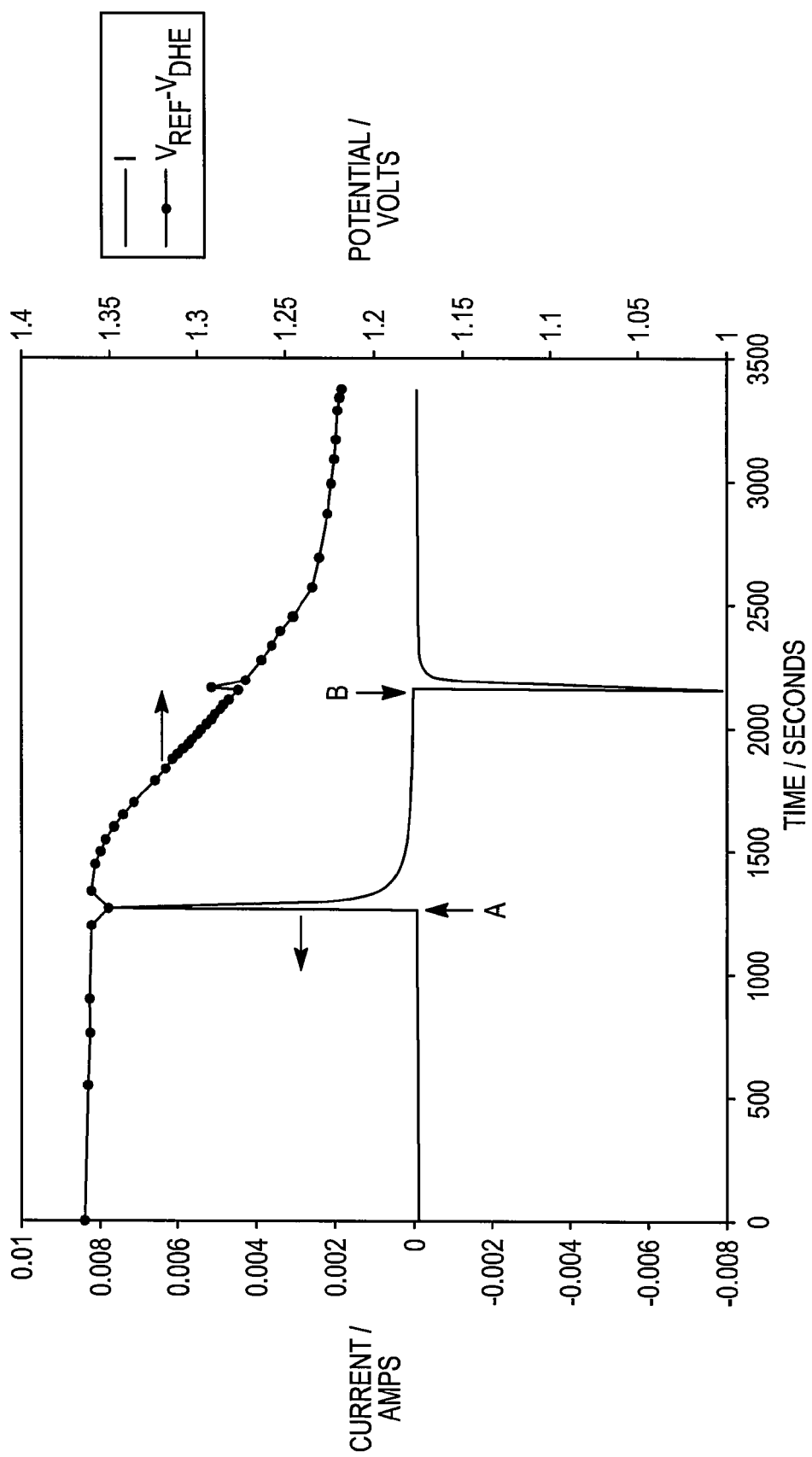
FIG. 2 is a graph which illustrates aspects of a method in accordance with the invention.

FIG. 2 illustrates aspects of a procedure that was used to 'clean up' the sensor in FIG. 1. The solid line illustrates the sensor current. The line with circles illustrates the potential of the platinum pseudoreference electrode measured relative to an external reference (dynamic hydrogen electrode)—note that in normal use this external reference electrode would not be present.

At the beginning of the process the working electrode can be initially biased at −600 mV relative to the platinum pseudoreference electrode. At point 'A' the working electrode bias is switched to 0V, resulting in a large current transient and corresponding swing in counter electrode potential. It can be seen that the pseudoreference electrode potential now begins to shift negatively, back towards its 'ideal' operating potential.

At point 'B' the working electrode bias is returned to its normal operating value of −600 mV relative to the pseudoreference electrode, however as the potential of the latter has become more negative by about 150 mV, in reality the working electrode is now operating at a more negative electrochemical potential than before, recovering its activity and hence speed of response to its 'correct' operating level.

Figure 3A:
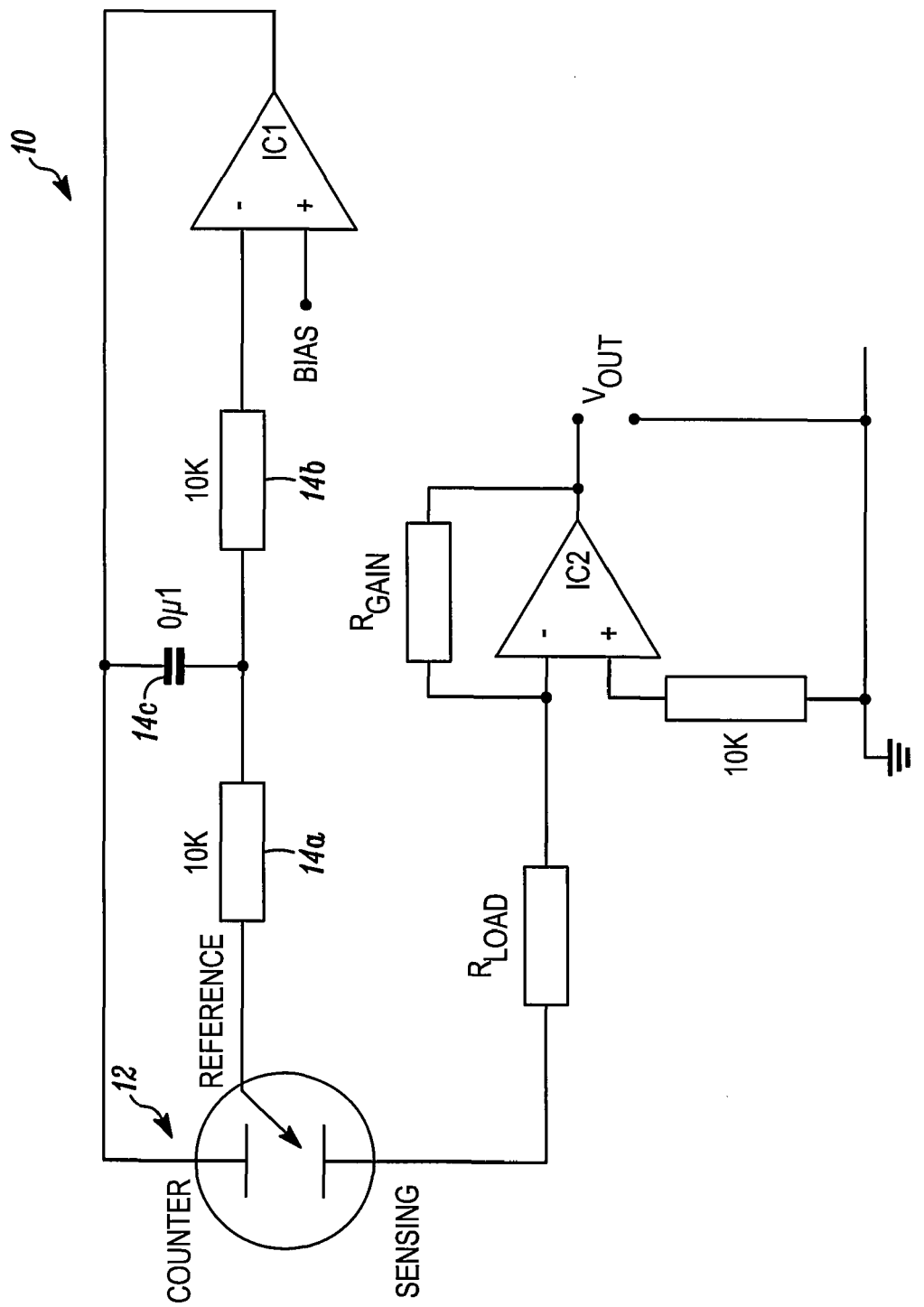
FIG. 3A is a block diagram of an exemplary apparatus for practicing a method in accordance with the invention.

FIG. 3A illustrates a block diagram of an apparatus which can be used to practice the above described method. The circuit 10 of FIG. 3A is a conventional potentiostatic circuit as commonly used for three electrode electrochemical sensors, such as sensor 12. The circuit 10 includes integrated circuit IC1 and its associated resistors 14a, b and capacitor 14c, which may be included for stability.

The circuit IC2 is configured as a current follower and is used to provide an output voltage Vout proportional the sensor current. Resistor RLoad is optional. The circuit 10 effectively adjusts the potential applied to the counter electrode so as to maintain a specified potential between the reference electrode and sensor, or, working electrode, defined by the bias voltage applied to IC1.

Those of skill in the art will understand that the circuit elements of the circuit 10 can be carried in a common housing with electrode 12. Alternately, elements such as the circuit 10 could be replicated in a docking/test station and intermittently coupled to a gas sensing cell, such as the cell 12.

One method of implementing the invention is to change the bias voltage such that the counter electrode swings to a potential, relative to the reference electrode, similar to that at which the working electrode normally operates.

Figure 3B:
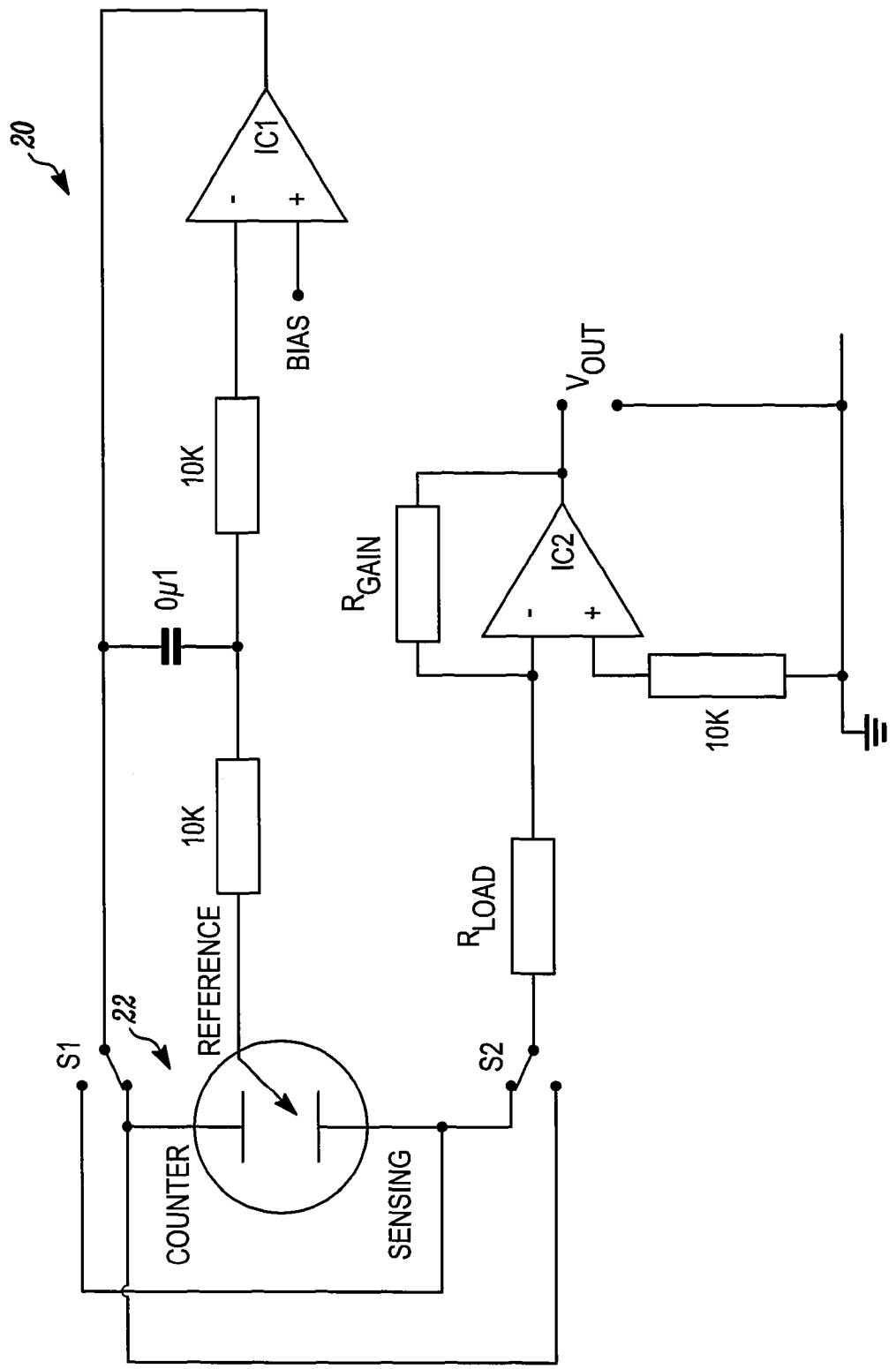
FIG. 3B is another block diagram of a different exemplary apparatus for practicing a method in accordance with the invention.

Another method of implementing the invention is shown in FIG. 3B. Here in apparatus 20, the connections to the working and counter electrodes of an electrochemical gas sensing cell 22 are physically reversed by simultaneously operating switches S1 and S2. Thus, a bias voltage can be applied to the counter electrode, relative to the reference electrode, while using the usual sensing electrode as a counter electrode. The switching elements, may be, for example, implemented as a mechanical switch, relay or a suitable solid state switch.

In summary, a method of processing an electro-chemical gas responsive cell, having at least first and second electrodes, can include establishing a selected electrode to be treated; and, applying a potential to at least one different electrode to modify one of, the properties of, or the environment around the selected electrode to thereby treat the selected electrode so that the cell exhibits improved performance. In other aspects of the invention, where the cell has at least three electrodes, a voltage can be coupled across two of the three, in the absence of current flowing to/from the third electrode, to modify one of, the properties of, or the environment around the third electrode.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A method improving a relative sensitivity of an electrochemical gas responsive cell having a working electrode, a counter electrode and a reference electrode where said electro-chemical cell has become degraded by use over time by an interferent gas generated by or incompletely consumed by the working electrode, the method comprising:
    establishing a first bias configuration relative to the electrodes of the cell, and biasing a working electrode to a first value;
    switching the working electrode or counter electrode that generated or incompletely consumed the interferent gas to a second, different bias value for a predetermined time period to remove the generated or incompletely consumed interferent gas dissolved in an electrolyte around the reference electrode; and
    returning the working electrode to its first bias value.

2. A method as in claim 1 where biasing to the first value comprises biasing to a value on the order of −600 mv relative to a selected reference.

3. A method as in claim 1 where switching includes switching to a value on the order of zero volts.

4. A method as in claim 1 where the cell comprises an oxygen responsive cell.

5. A method as in claim 1 where the cell has at least three electrodes and where the environment around the third electrode is modified to improve the response parameter of the cell to the selected gas.

6. A method of improving a relative sensitivity of an electrochemical gas responsive cell having three electrodes where said electrochemical gas responsive cell has become degraded by use over time via an interferent gas generated by or incompletely consumed by a first or second of the three electrodes comprising:
    applying a voltage to one of the first or second electrodes to thereby alter characteristics of the environment of a third of the three electrodes by removing the generated or incompletely consumed interferent gas dissolved in an electrolyte around the third electrode, and,
    simultaneously with applying the voltage, avoiding passing a current through the third electrode.

7. A method as in claim 6 which includes applying the voltage to at least one of a working electrode or a counter electrode.

8. A method as in claim 7 where the cell has at least three electrodes and which includes applying the voltage across two of the electrodes in the absence of current flowing into, or from the third electrode.

* * * * *